US011941806B2

(12) United States Patent
Pardasani et al.

(10) Patent No.: US 11,941,806 B2
(45) Date of Patent: Mar. 26, 2024

(54) METHODS AND SYSTEMS FOR AUTOMATIC ASSESSMENT OF FRACTIONAL LIMB VOLUME AND FAT LEAN MASS FROM FETAL ULTRASOUND SCANS

(71) Applicant: GE Precision Healthcare LLC, Wauwatosa, WI (US)

(72) Inventors: Rohit Pardasani, Bengaluru (IN); Hrithik Auchar, Bengaluru (IN)

(73) Assignee: GE Precision Healthcare LLC, Waukesha, WI (US)

( * ) Notice: Subject to any disclaimer, the term of this patent is extended or adjusted under 35 U.S.C. 154(b) by 354 days.

(21) Appl. No.: 17/477,909

(22) Filed: Sep. 17, 2021

(65) Prior Publication Data

US 2023/0087363 A1 Mar. 23, 2023

(51) Int. Cl.
| | |
|---|---|
| *G06T 7/00* | (2017.01) |
| *G06T 7/11* | (2017.01) |
| *G06T 7/149* | (2017.01) |
| *G16H 50/20* | (2018.01) |
| *G16H 50/30* | (2018.01) |

(52) U.S. Cl.
CPC ............ *G06T 7/0012* (2013.01); *G06T 7/11* (2017.01); *G06T 7/149* (2017.01); *G16H 50/20* (2018.01); *G16H 50/30* (2018.01); *G06T 2207/20081* (2013.01); *G06T 2207/20084* (2013.01); *G06T 2207/30008* (2013.01); *G06T 2207/30044* (2013.01)

(58) Field of Classification Search
None
See application file for complete search history.

(56) References Cited

U.S. PATENT DOCUMENTS

| | | | |
|---|---|---|---|
| 6,375,616 B1 | 4/2002 | Soferman et al. | |
| 7,004,904 B2 | 2/2006 | Chalana et al. | |
| 2021/0298717 A1* | 9/2021 | Rouet | ................... G06T 7/0014 |

OTHER PUBLICATIONS

Fetal Weight Estimation Using Automated Fractional Limb Volume With 2-Dimensional Size Parameters (Wesley Lee MD, 2020).

(Continued)

*Primary Examiner* — Leon Flores
(74) *Attorney, Agent, or Firm* — McAndrews, Held & Malloy, Ltd.; Daniel Bissing; David Bates

(57) ABSTRACT

Automated assessment for a fetus may be applied based on imaging data obtained during medical imaging examination of the fetus, with the applying including processing imaging data corresponding to a plurality of a cross-section imaging slices corresponding to a limb of the fetus, where the processing includes for each imaging slice: automatically generating a predicted outer mask for an outer contour of the limb based on application of a first pre-trained model to imaging data corresponding to the imaging slice; and automatically generating a segmentation of fat-lean mask for the imaging slice based on application of a second pre-trained model to both of the imaging data corresponding to the imaging slice and the generated predicted output mask; and applying based on the processing of the imaging data corresponding to the plurality of a cross-section imaging slices: a fractional limb volume assessment; and a fat-lean mass assessment.

20 Claims, 6 Drawing Sheets

(56) References Cited

OTHER PUBLICATIONS

"Automatic Fetal Weight Estimation Using 3D Ultrosonography" (Feng S, 2015).
Birth Weight and Neonatal Adiposity Prediction Using Fractional Limb Volume Obtained with 3D Ultrasound (link) (Connor, et al., 2016).
Semiautomatic Assessment of Fetal Fractional Limb Volume for Weight Prediction in Clinical Praxis (link) (Gembicki, Offerman, & Weichert, 2021).
Birth-weight prediction using three dimensional sonographic fractional thigh volume at term in a Chinese population (link) (Yang, Leung, Hous, Yuan, & Tang, 2011).
"Fractional limb volume—a soft tissue parameter of fetal body composition: validation, technical considerations and normal ranges during pregnancy", W. Lee, et al., Ultrasound Obstet Gynecol 2009; 33: 427-440 Published online Feb. 27, 2009 in Wiley InterScience (www.interscience.wiley.com). DOI: 10.1002/uog.6319, pp. 427-440.
Automated Fractional Limb Volume Measurements Improve the Precision of Birth Weight Predictions in Late Third Trimester Fetuses (Mack, Sung, Sungmin, Sangi, & Lee, 2017).
"BB-UNet: U-Net with Bounding Box Prior", Rosana El Jurdi, Caroline Petitjean, Paul Honeine, Fahed Abdallah, University of Exeter, downloaded on Jul. 1, 2020 from IEEE Xplore, (10 pages).
"Why is Fetal Soft Tissue Assessment Important?", Wesley Lee, M.D., OB/GYN Ultrasound Symposium 2018, Sep. 28-30, 2018, UChicago Medicine ,(20 pages).

* cited by examiner

METHODS AND SYSTEMS FOR AUTOMATIC ASSESSMENT OF FRACTIONAL LIMB VOLUME AND FAT LEAN MASS FROM FETAL ULTRASOUND SCANS

FIELD

Aspects of the present disclosure relate to medical imaging solutions. More specifically, certain embodiments relate to methods and systems for automatic assessment of fractional limb volume and fat lean mass from fetal ultrasound scans.

BACKGROUND

Various medical imaging techniques may be used, such as in imaging organs and soft tissues in a human body. Examples of medical imaging techniques include ultrasound imaging, computed tomography (CT) scans, magnetic resonance imaging (MRI), etc. The manner by which images are generated during medical imaging depends on the particular technique.

For example, ultrasound imaging uses real time, non-invasive high frequency sound waves to produce ultrasound images, typically of organs, tissues, objects (e.g., fetus) inside the human body. Images produced or generated during medical imaging may be two-dimensional (2D), three-dimensional (3D), and/or four-dimensional (4D) images (essentially real-time/continuous 3D images). During medical imaging, imaging datasets (including, e.g., volumetric imaging datasets during 3D/4D imaging) are acquired and used in generating and rendering corresponding images (e.g., via a display) in real-time.

Use of medical imaging systems in conjunction with certain types of examination, however, may pose certain challenges, particularly with respect to assessing outcome of the examination. For example, in some examinations assessing health of fetus based on medical imaging may be difficult, time-consuming, and not sufficiently reliable. Limitations and disadvantages of conventional approaches, if any existed, for handling such situations will become apparent to one of skill in the art, through comparison of such approaches with some aspects of the present disclosure, as set forth in the remainder of the present application with reference to the drawings.

BRIEF SUMMARY

System and methods are provided for automatic assessment of fractional limb volume and fat lean mass from fetal ultrasound scans, substantially as shown in and/or described in connection with at least one of the figures, as set forth more completely in the claims.

These and other advantages, aspects and novel features of the present disclosure, as well as details of one or more illustrated example embodiments thereof, will be more fully understood from the following description and drawings.

DETAILED DESCRIPTION

Figure 1:
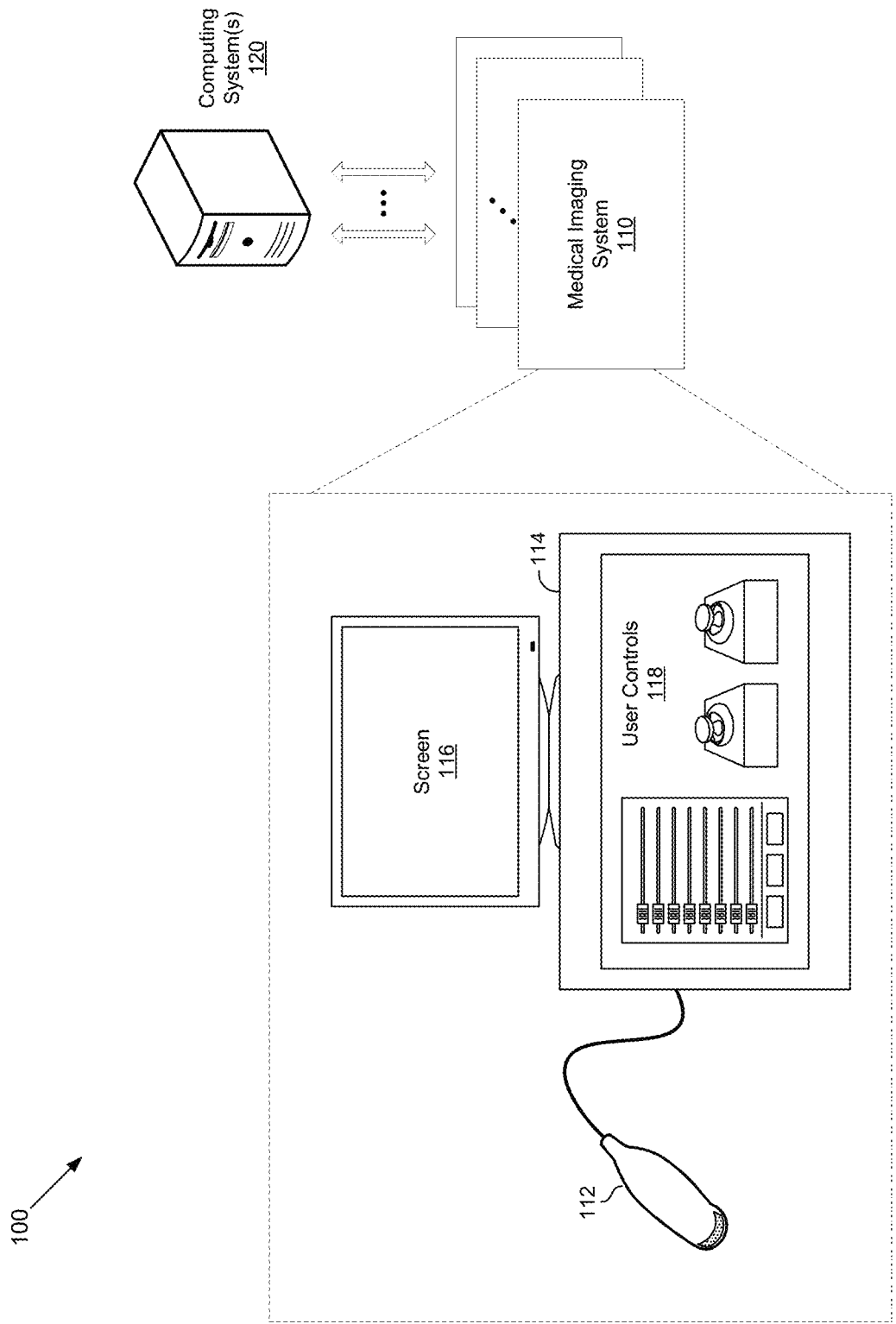
FIG. 1 is a block diagram illustrating an example medical imaging arrangement.

Certain implementations in accordance with the present disclosure may be directed to automatic assessment of fractional limb volume and fat lean mass from fetal ultrasound scans. The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" as used in the context of ultrasound imaging is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

In addition, as used herein, the phrase "pixel" also includes embodiments where the data is represented by a "voxel." Thus, both the terms "pixel" and "voxel" may be used interchangeably throughout this document.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC, or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". In addition, forming of images may be performed using channel combinations that may originate from more than one transmit event (e.g., synthetic aperture techniques).

Figure 2:
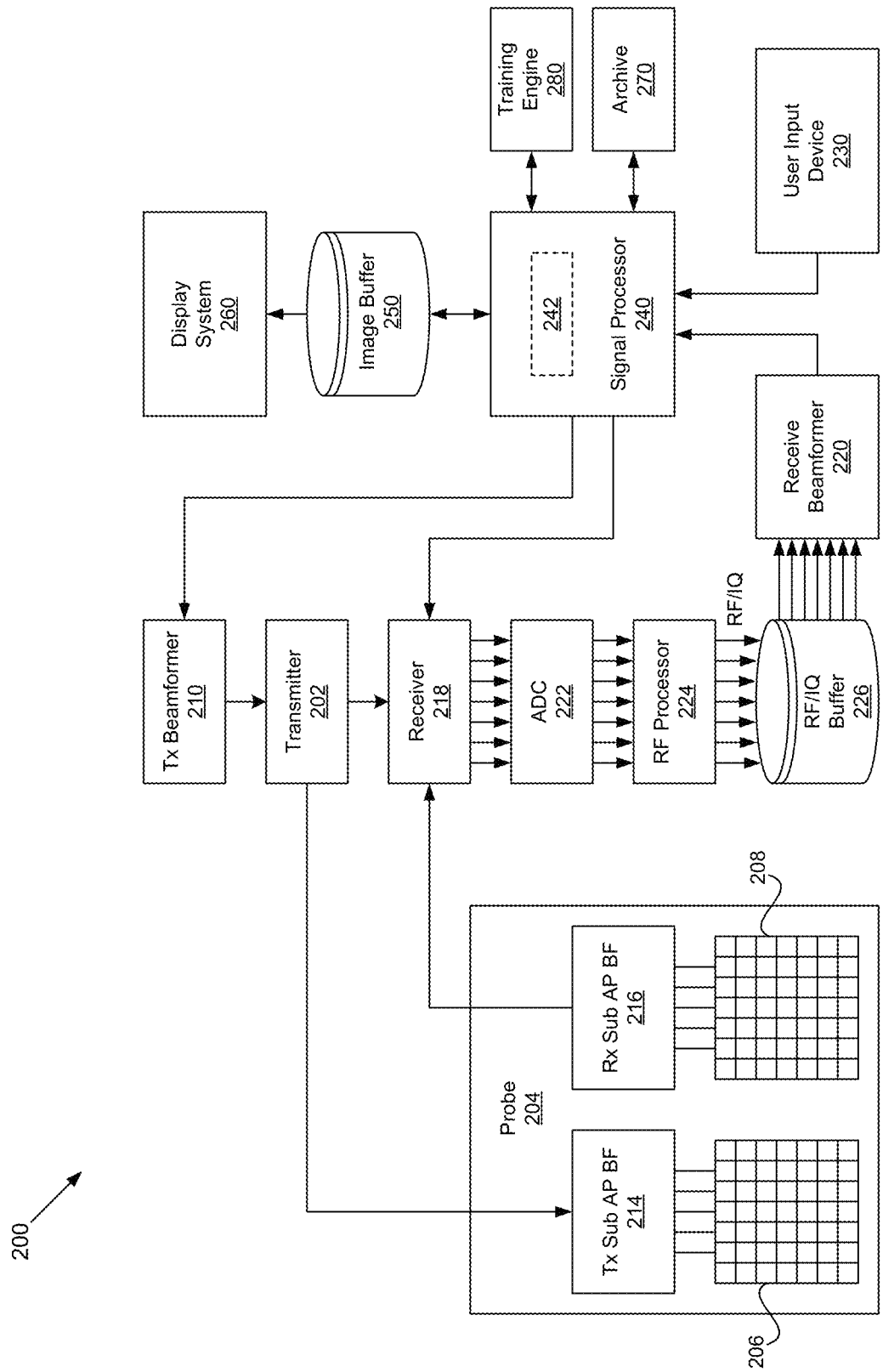
FIG. 2 is a block diagram illustrating an example ultrasound system.

In various embodiments, processing to form images is performed in software, firmware, hardware, or a combination thereof. The processing may include use of beamforming. One example implementation of an ultrasound system having a software beamformer architecture formed in accordance with various embodiments as illustrated in FIG. 2.

The medical imaging system 110 comprise suitable hardware, software, or a combination thereof, for supporting medical imaging—that is enabling obtaining data used in generating and/or rendering images during medical imaging exams. Examples of medical imaging include ultrasound imaging, computed tomography (CT) scans, magnetic resonance imaging (MRI), etc. This may entail capturing of particular type of data, in particular manner, which may in turn be used in generating data for the images. For example, the medical imaging system 110 may be an ultrasound imaging system, configured for generating and/or rendering ultrasound images. An example implementation of an ultrasound system, which may correspond to the medical imaging system 110, is described in more detail with respect to FIG. 2.

As shown in FIG. 1, the medical imaging system 110 may comprise a scanner device 112, which may be portable and movable, and a display/control unit 114. The scanner device 112 may be configured for generating and/or capturing particular type of imaging signals (and/or data corresponding thereto), such as by being moved over a patient's body (or part thereof), and may comprise suitable circuitry for performing and/or supporting such functions. The scanner device 112 may be an ultrasound probe, MRI scanner, CT scanner, or any suitable imaging device. For example, where the medical imaging system 110 is an ultrasound system, the scanner device 112 may emit ultrasound signals and capture echo ultrasound images.

The display/control unit 114 may be configured for displaying images (e.g., via a screen 116). In some instances, the display/control unit 114 may further be configured for generating the displayed images, at least partly. Further, the display/control unit 114 may also support user input/output. For example, the display/control unit 114 may provide (e.g., via the screen 116), in addition to the images, user feedback (e.g., information relating to the system, functions thereof, settings thereof, etc.). The display/control unit 114 may also support user input (e.g., via user controls 118), such as to allow controlling of the medical imaging. The user input may be directed to controlling display of images, selecting settings, specifying user preferences, requesting feedback, etc.

In some implementations, the medical imaging arrangement 100 may also incorporate additional and dedicated computing resources, such as the one or more computing systems 120. In this regard, each computing system 120 may comprise suitable circuitry, interfaces, logic, and/or code for processing, storing, and/or communication data. The computing system 120 may be dedicated equipment configured particularly for use in conjunction with medical imaging, or it may be a general purpose computing system (e.g., personal computer, server, etc.) set up and/or configured to perform the operations described hereinafter with respect to the computing system 120. The computing system 120 may be configured to support operations of the medical imaging systems 110, as described below. In this regard, various functions and/or operations may be offloaded from the imaging systems. This may be done to streamline and/or centralize certain aspects of the processing, to reduce cost—e.g., by obviating the need to increase processing resources in the imaging systems.

The computing systems 120 may be set up and/or arranged for use in different ways. For example, in some implementations a single computing system 120 may be used; in other implementations multiple computing systems 120, either configured to work together (e.g., based on distributed-processing configuration), or separately, with each computing system 120 being configured to handle particular aspects and/or functions, and/or to process data only for particular medical imaging systems 110. Further, in some implementations, the computing systems 120 may be local (e.g., co-located with one or more medical imaging systems 110, such within the same facility and/or same local network); in other implementations, the computing systems 120 may be remote and thus can only be accessed via remote connections (e.g., via the Internet or other available remote access techniques). In a particular implementation, the computing systems 120 may be configured in cloud-based manner, and may be accessed and/or used in substantially similar way that other cloud-based systems are accessed and used.

Once data is generated and/or configured in the computing system 120, the data may be copied and/or loaded into the medical imaging systems 110. This may be done in different ways. For example, the data may be loaded via directed connections or links between the medical imaging systems 110 and the computing system 120. In this regard, communications between the different elements in the medical imaging arrangement 100 may be done using available wired and/or wireless connections, and/or in accordance any suitable communication (and/or networking) standards or protocols. Alternatively, or additionally, the data may be loaded into the medical imaging systems 110 indirectly. For example, the data may be stored into suitable machine readable media (e.g., flash card, etc.), which are then used to load the data into the medical imaging systems 110 (on-site, such as by users of the systems (e.g., imaging clinicians) or authorized personnel), or the data may be downloaded into local communication-capable electronic devices (e.g., laptops, etc.), which are then used on-site (e.g., by users of the systems or authorized personnel) to upload the data into the medical imaging systems 110, via direct connections (e.g., USB connector, etc.).

In operation, the medical imaging system 110 may be used in generating and presenting (e.g., rendering or displaying) images during medical exams, and/or in supporting user input/output in conjunction therewith. The images may be 2D, 3D, and/or 4D images. The particular operations or functions performed in the medical imaging system 110 to facilitate the generating and/or presenting of images depends on the type of system—that is, the manner by which the data corresponding to the images is obtained and/or generated. For example, in computed tomography (CT) scans based imaging, the data is based on emitted and captured x-rays signals. In ultrasound imaging, the data is based on emitted and echo ultrasound signals. This described in more details with respect to the example ultrasound-based implementation illustrated in and described with respect to FIG. 2.

In various implementations in accordance with the present disclosure, medical imaging systems and/or architectures (e.g., the medical imaging system 110 and/or the medical imaging arrangement 100 as a whole) may be configured to support automatic assessment of fractional limb volume and fat lean mass from fetal medical imaging (e.g., ultrasound based imaging). Fractional limb volume and fat lean mass may be used to assess the size and health of fetus, particularly during the later stages (e.g., third trimester) of pregnancy. In this regard, fetuses may be examined using conventional sonography for the clinical estimation of weight and evaluating prenatal nutritional status. In current obstetric practice an estimation of fetal size, based on various measurements obtained from medical images (e.g., 3D ultrasound images) may be used as common means of evaluating prenatal nutritional status. However, conventional solutions that may be utilized in conjunction with obtaining and/or making such assessments (e.g., in determining, estimating, and/or assessing parameters used for such assessments) may have various limitations and/or may pose some challenges.

For example, the conventional approach may not allow for precisely separating malnourished fetuses from those that are constitutionally small or large, but otherwise normal. For instance, most prediction models that may be used in convention solutions may not include soft tissue parameters for fetal weight estimation due to technical limitations. Thus, including soft tissue parameters can significantly improve the neonatal assessment and make it more robust. Further, fetuses with intrauterine growth restriction could also be diagnosed after considering soft tissue parameters since they have reduced subcutaneous fat and lean body mass compared to normal controls.

Other limitations that may exist in conventional solutions may stem from the complexity of the required assessments associated therewith. For example, manual assessment of ultrasound scans is a laborious and time-consuming process. Estimation of fetal weight is done based on fetal ultrasound biometry and birth weight is calculated according to these values by using published formulas from different authors for different ethnicities. However, all the formulas using normal biometry may not work well in some instances, such as with overweight or underweight babies because the conventional methods may not take in to account the soft tissue parameter leading to inaccurate weight estimation.

Solutions in accordance with the present disclosure may overcome or otherwise mitigate at least some of the limitations or issues associated with convention solutions. In particular, in various implementations an automatic estimation of fractional limb volume and fat lean mass from fetal medical image (e.g., 3D ultrasound scans) may be used. The automation may be implemented using deep learning approach, to further enhance performance—e.g., reducing workload on users, and/or reducing unreliability of results. Thus, fractional limb volume and fat lean mass as evaluated based on the automated estimation may be used more effectively and reliably in assessing the nutritional and health status of the fetus. The solutions and example implementations associated therewith are described in more details below.

For example, ultrasound scans of fetal limb cross-sections may be analyzed, and fat and lean mass may be identified, followed by the estimation of fat mass volume and lean mass volume. Thus, the automated estimation would provide not only an estimate of fractional limb volume, but also the portion of fat mass and lean mass for that fractional limb volume, which may significantly improve understanding of fetal development. These parameters may further be used for accurate birth weight estimation as well as to facilitate and/or assist with other fetal related determinations. For example, the automated assessment, and parameters obtained based thereon, may help to identify more reliably and accurate which baby may be at risk for Large for gestational age (LGA) or Small for gestational age (SGA). Several other maternal and fetal health risks that are associated with the nutritional status (e.g., macrosomia, fetuses with intra uterine growth restrictions) may also be identified more reliably and accurately. The solutions and example implementations associated therewith are described in more details below.

FIG. 2 is a block diagram illustrating an example ultrasound imaging system. Shown in FIG. 2 is an ultrasound imaging system 200, which may be configured to support automatic assessment of fractional limb volume and fat lean mass from fetal ultrasound scans in accordance with the present disclosure.

The ultrasound imaging system 200 may be configured for providing ultrasound imaging, and as such may comprise suitable circuitry, interfaces, logic, and/or code for performing and/or supporting ultrasound imaging related functions. The ultrasound imaging system 200 may correspond to the medical imaging system 110 of FIG. 1. The ultrasound imaging system 200 comprises, for example, a transmitter 202, an ultrasound probe 204, a transmit beamformer 210, a receiver 218, a receive beamformer 220, a RF processor 224, a RF/IQ buffer 226, a user input module 230, a signal processor 240, an image buffer 250, a display system 260, an archive 270, and a training engine 280.

The transmitter 202 may comprise suitable circuitry, interfaces, logic, and/or code that may be operable to drive an ultrasound probe 204. The ultrasound probe 204 may comprise a two dimensional (2D) array of piezoelectric elements. The ultrasound probe 204 may comprise a group of transmit transducer elements 206 and a group of receive transducer elements 208, that normally constitute the same elements. In certain embodiment, the ultrasound probe 204 may be operable to acquire ultrasound image data covering at least a substantial portion of an anatomy, such as the heart, a blood vessel, or any suitable anatomical structure.

The transmit beamformer 210 may comprise suitable circuitry, interfaces, logic, and/or code that may be operable to control the transmitter 202 which, through a transmit sub-aperture beamformer 214, drives the group of transmit transducer elements 206 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 208.

The group of receive transducer elements 208 in the ultrasound probe 204 may be operable to convert the received echoes into analog signals, undergo sub-aperture beamforming by a receive sub-aperture beamformer 216 and are then communicated to a receiver 218. The receiver 218 may comprise suitable circuitry, interfaces, logic, and/or code that may be operable to receive the signals from the receive sub-aperture beamformer 216. The analog signals may be communicated to one or more of the plurality of A/D converters 222.

The plurality of A/D converters 222 may comprise suitable circuitry, interfaces, logic, and/or code that may be operable to convert the analog signals from the receiver 218 to corresponding digital signals. The plurality of A/D converters 222 are disposed between the receiver 218 and the RF processor 224. Notwithstanding, the disclosure is not limited in this regard. Accordingly, in some embodiments, the plurality of A/D converters 222 may be integrated within the receiver 218.

The RF processor 224 may comprise suitable circuitry, interfaces, logic, and/or code that may be operable to demodulate the digital signals output by the plurality of A/D converters 222. In accordance with an embodiment, the RF processor 224 may comprise a complex demodulator (not shown) that is operable to demodulate the digital signals to form I/Q data pairs that are representative of the corresponding echo signals. The RF or I/Q signal data may then be communicated to an RF/IQ buffer 226. The RF/IQ buffer 226 may comprise suitable circuitry, interfaces, logic, and/or code that may be operable to provide temporary storage of the RF or I/Q signal data, which is generated by the RF processor 224.

The receive beamformer 220 may comprise suitable circuitry, interfaces, logic, and/or code that may be operable to perform digital beamforming processing to, for example, sum the delayed channel signals received from RF processor 224 via the RF/IQ buffer 226 and output a beam summed signal. The resulting processed information may be the beam summed signal that is output from the receive beamformer 220 and communicated to the signal processor 240. In accordance with some embodiments, the receiver 218, the plurality of A/D converters 222, the RF processor 224, and the beamformer 220 may be integrated into a single beamformer, which may be digital. In various embodiments, the ultrasound imaging system 200 comprises a plurality of receive beamformers 220.

The user input device 230 may be utilized to input patient data, scan parameters, settings, select protocols and/or templates, interact with an artificial intelligence segmentation processor to select tracking targets, and the like. In an example embodiment, the user input device 230 may be operable to configure, manage and/or control operation of one or more components and/or modules in the ultrasound imaging system 200. In this regard, the user input device 230 may be operable to configure, manage and/or control operation of the transmitter 202, the ultrasound probe 204, the transmit beamformer 210, the receiver 218, the receive beamformer 220, the RF processor 224, the RF/IQ buffer 226, the user input device 230, the signal processor 240, the image buffer 250, the display system 260, archive 270, and/or the training engine 280.

For example, the user input device 230 may include button(s), rotary encoder(s), a touchscreen, motion tracking, voice recognition, a mouse device, keyboard, camera and/or any other device capable of receiving user directive(s). In certain embodiments, one or more of the user input devices 230 may be integrated into other components, such as the display system 260 or the ultrasound probe 204, for example.

As an example, user input device 230 may include a touchscreen display. As another example, user input device 230 may include an accelerometer, gyroscope, and/or magnetometer attached to and/or integrated with the probe 204 to provide gesture motion recognition of the probe 204, such as to identify one or more probe compressions against a patient body, a pre-defined probe movement or tilt operation, or the like. In some instances, the user input device 230 may include, additionally or alternatively, image analysis processing to identify probe gestures by analyzing acquired image data. In accordance with the present disclosure, the user input and functions related thereto may be configured to support use of new data storage scheme, as described in this disclosure. For example, the user input device 230 may be configured to support receiving user input directed at triggering and managing (where needed) application of separation process, as described herein, and/or to provide or set parameters used in performing such process. Similarly, the user input device 230 may be configured to support receiving user input directed at triggering and managing (where needed) application of the recovery process, as described herein, and/or to provide or set parameters used in performing such process.

The signal processor 240 may comprise suitable circuitry, interfaces, logic, and/or code that may be operable to process ultrasound scan data (i.e., summed IQ signal) for generating ultrasound images for presentation on a display system 260. The signal processor 240 is operable to perform one or more processing operations according to a plurality of selectable ultrasound modalities on the acquired ultrasound scan data. In an example embodiment, the signal processor 240 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 226 during a scanning session and processed in less than real-time in a live or off-line operation. In various embodiments, the processed image data can be presented at the display system 260 and/or may be stored at the archive 270.

The archive 270 may be a local archive, a Picture Archiving and Communication System (PACS), or any suitable device for storing images and related information, or may be coupled to such device or system for facilitating the storage and/or achieving of the imaging related data. In an example implementation, the archive 270 is further coupled to a remote system such as a radiology department information system, hospital information system, and/or to an internal or external network (not shown) to allow operators at different locations to supply commands and parameters and/or gain access to the image data.

The signal processor 240 may be one or more central processing units, microprocessors, microcontrollers, and/or the like. The signal processor 240 may be an integrated component, or may be distributed across various locations, for example. The signal processor 240 may be configured for receiving input information from the user input device 230 and/or the archive 270, generating an output displayable by the display system 260, and manipulating the output in response to input information from the user input device 230, among other things. The signal processor 240 may be capable of executing any of the method(s) and/or set(s) of instructions discussed herein in accordance with the various embodiments, for example.

The ultrasound imaging system 200 may be operable to continuously acquire ultrasound scan data at a frame rate that is suitable for the imaging situation in question. Typical frame rates range from 20-220 but may be lower or higher. The acquired ultrasound scan data may be displayed on the display system 260 at a display-rate that can be the same as the frame rate, or slower or faster. The image buffer 250 is included for storing processed frames of acquired ultrasound scan data that are not scheduled to be displayed immediately. Preferably, the image buffer 250 is of sufficient capacity to store at least several minutes' worth of frames of ultrasound scan data. The frames of ultrasound scan data are stored in a manner to facilitate retrieval thereof according to its order or time of acquisition. The image buffer 250 may be embodied as any known data storage medium.

In an example embodiment, the signal processor 240 may comprise an automated fetal analysis module 242, which comprises suitable circuitry, interfaces, logic, and/or code that may be configured to perform and/or support various functions or operations relating to, or in support of automatic assessment of fractional limb volume and fat lean mass from fetal ultrasound scans, as described in this disclosure.

In some implementations, the signal processor 240 (and/or components thereof, such as the automated fetal analysis module 242) may be configured to implement and/or use artificial intelligence and/or machine learning techniques to enhance and/or optimize imaging related functions or operations. For example, the signal processor 240 (and/or components thereof, such as the automated fetal analysis module 242) may be configured to implement and/or use deep learning techniques and/or algorithms, such as by use of deep neural networks (e.g., a convolutional neural network (CNN)), and/or may utilize any suitable form of artificial intelligence based processing techniques or machine learning processing functionality (e.g., for image analysis). Such artificial intelligence based image analysis may be configured to, e.g., analyze acquired ultrasound images, such as to identify, segment, label, and track structures (or tissues thereof) meeting particular criteria and/or having particular characteristics.

In an example implementation, the signal processor 240 (and/or components thereof, such as the automated fetal analysis module 242) may be provided as a deep neural network, which may be made up of, for example, an input layer, an output layer, and one or more hidden layers in between the input and output layers. Each of the layers may be made up of a plurality of processing nodes that may be referred to as neurons.

For example, the deep neural network may include an input layer having a neuron for each pixel or a group of pixels from a scan plane of an anatomical structure, and the output layer may have a neuron corresponding to a plurality of pre-defined structures or types of structures (or tissue(s) therein). Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The neurons of a fourth layer may learn characteristics of particular tissue types present in particular structures, etc. Thus, the processing performed by the deep neural network (e.g., convolutional neural network (CNN)) may allow for identifying biological and/or artificial structures in ultrasound image data with a high degree of probability.

In some implementations, the signal processor 240 (and/or components thereof, such as the automated fetal analysis module 242) may be configured to perform or otherwise control at least some of the functions performed thereby based on a user instruction via the user input device 230. As an example, a user may provide a voice command, probe gesture, button depression, or the like to issue a particular instruction, such as to initiate and/or control various aspects of the new data management scheme, including artificial intelligence (AI) based operations, and/or to provide or otherwise specify various parameters or settings relating thereto, as described in this disclosure.

The training engine 280 may comprise suitable circuitry, interfaces, logic, and/or code that may be operable to train the neurons of the deep neural network(s) of the signal processor 240 (and/or components thereof, such as the automated fetal analysis module 242). For example, the signal processor 240 may be trained to identify particular structures and/or tissues (or types thereof) provided in an ultrasound scan plane, with the training engine 280 training the deep neural network(s) thereof to perform some of the required functions, such as using databases(s) of classified ultrasound images of various structures.

As an example, the training engine 280 may be configured to utilize ultrasound images to train the signal processor 240 (and/or components thereof, such as the automated fetal analysis module 242), such as based on particular structure (s) and/or characteristics thereof, particular tissues and/or characteristics thereof, etc. For example, with the respect to structure(s), the training engine 280 may be configured to identify and utilize such characteristics as appearance of structure edges, appearance of structure shapes based on the edges, positions of the shapes relative to landmarks in the ultrasound image data, and the like. In various embodiments, the databases of training images may be stored in the archive 270 or any suitable data storage medium. In certain embodiments, the training engine 280 and/or training image databases may be external system(s) communicatively coupled via a wired or wireless connection to the ultrasound imaging system 200.

In operation, the ultrasound imaging system 200 may be used in generating ultrasonic images, including two-dimensional (2D), three-dimensional (3D), and/or four-dimensional (4D) images. In this regard, the ultrasound imaging system 200 may be operable to continuously acquire ultrasound scan data at a particular frame rate, which may be suitable for the imaging situation in question. For example, frame rates may range from 30-70 but may be lower or higher. The acquired ultrasound scan data may be displayed on the display system 260 at a display-rate that can be the same as the frame rate, or slower or faster. An image buffer 250 is included for storing processed frames of acquired ultrasound scan data not scheduled to be displayed immediately. Preferably, the image buffer 250 is of sufficient capacity to store at least several seconds' worth of frames of ultrasound scan data. The frames of ultrasound scan data are stored in a manner to facilitate retrieval thereof according to its order or time of acquisition. The image buffer 250 may be embodied as any known data storage medium.

In some instances, the ultrasound imaging system 200 may be configured to support grayscale and color based operations. For example, the signal processor 240 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope can undergo additional B-mode processing, such as logarithmic compression to form the display data.

The display data may be converted to X-Y format for video display. The scan-converted frames can be mapped to grayscale for display. The B-mode frames that are provided to the image buffer 250 and/or the display system 260. The color processing may comprise processing color based RF signal data or IQ data pairs to form frames to overlay on B-mode frames that are provided to the image buffer 250 and/or the display system 260. The grayscale and/or color processing may be adaptively adjusted based on user input—e.g., a selection from the user input device 230, for example, for enhance of grayscale and/or color of particular area.

In some instances, ultrasound imaging may include generation and/or display of volumetric ultrasound images—that is where objects (e.g., organs, tissues, etc.) are displayed three-dimensional 3D. In this regard, with 3D (and similarly 4D) imaging, volumetric ultrasound datasets may be acquired, comprising voxels that correspond to the imaged objects. This may be done, e.g., by transmitting the sound waves at different angles rather than simply transmitting them in one direction (e.g., straight down), and then capture their reflections back. The returning echoes (of transmissions at different angles) are then captured, and processed (e.g., via the signal processor 240) to generate the corresponding volumetric datasets, which may in turn be used in creating and/or displaying volume (e.g. 3D) images, such as via the display 250. This may entail use of particular handling techniques to provide the desired 3D perception.

For example, volume rendering techniques may be used in displaying projections (e.g., 3D projections) of the volumetric (e.g., 3D) datasets. In this regard, rendering a 3D projection of a 3D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel.

In some embodiments, the ultrasound imaging system 200 may be configured to support automatic assessment of fractional limb volume and fat lean mass from fetal ultrasound scans in accordance with the present disclosure. In this regard, as noted use of fetal assessments based on fractional limb volume and fat lean mass (e.g., for evaluating size and health of fetus) may be desirable, particularly during the later stages (e.g., third trimester) of pregnancy. In particular, soft tissue (fat and lean mass) volume may be used to drastically improve fetal birth weight estimation and may significantly improve understanding on fetal growth. Solutions in accordance with the present disclosure may incorporate measures for quantifying fat and lean body mass, and doing so automatically, particularly based on medical three-dimensional (3D) ultrasound volumes acquired during 2nd and 3rd trimester. This may be done, for example, by identifying fat and lean mass portions of fractional arm and thigh volumes, such as based on 3D ultrasound scans.

In example implementation, volumes measurements may be based on, e.g., either 50% of humeral diaphysis length in fractional arm volume (AVol), or 50% of femoral diaphysis length in fractional thigh volume (TVol). Each partial volume may subdivided into a number (e.g., five) equidistant slices centered along the mid-arm or mid-thigh. This is explained in more detail with respect to FIGS. 3-5 below.

In accordance with the present disclosure, most of the assessments and related steps may be performed automatically, thus largely obviating the need for direct user action or control. Further, advanced processing techniques, such as artificial intelligence (AI) or other machine learning based techniques may be used. In this regard, since one of the primary objectives is identifying, as accurately as possible (and doing so in efficient manner), the fat mass and the lean mass regions in ultrasound images (e.g., in cross-section slices), this may be treated as a semantic segmentation task, which may be handled more optimally by use of artificial intelligence, such as deep learning algorithm and the like. In this regard, the ultrasound imaging system 200, particularly via the processor 240 (and/or components thereof, such as the automated fetal analysis module 242) may be configured to implement and/or support use of artificial intelligence (AI) based techniques in conjunction with the automated fetal assessment based solutions. For example, the automated fetal analysis module 242 (and the training engine 280) may be configured to support and use artificial intelligence (AI) based processing during automated fetal assessments, such as in conjunction with fractional limb volume assessment and/or fat-lean mass assessment. Alternatively or additionally, at least a portion of the artificial intelligence (AI) based learning mode related functions may be offloaded to an external system (e.g., local dedicated computing system, remote (e.g., Cloud-based) server, etc.).

As noted, identifying the fat mass and the lean mass regions in the cross-section slices may be treated as a semantic segmentation task. For example, cross-section slices may be manually annotated by skilled obstetrician to identify fat and lean portion in the ultrasound scans. The annotated regions may then be used train a deep learning algorithm in automatically identifying the fat and lean regions in the ultrasound cross-sections. For example, a U-Net, which is CNN encoder/decoder architecture, may be used to predict the fat and lean region in the ultrasound cross-section. The segmentation of the outer ring mass may happens in 2 steps: 1) prediction of limb region, and 2) prediction of the fat mass region.

In step 1 (prediction of limb region), a deep learning model (e.g., a U-Net architecture) may be trained to segment the entire limb region in the ultrasound image, resulting in an outer mask. The outer mask generated in this step will be further used in the next step for the segmentation of the fat mass region. In step 2 (prediction of the fat mass region), a second deep learning model (e.g., a second U-Net architecture) may be trained to segment the fat mass region—that is, the fat mass ring. In this regard, in step 2 the deep learning architecture learns to segment the fat ring mass based on the ultrasound image and the outer mask generated in step 1. After training the models are then assessed and evaluated on various performance metrics. Further, in some instances, post-processing maybe used to refine the segmentations made by the model to improve the segmentation.

The segmentation may then be used to compute the fat and the lean mass volumes, and these volumes may in turn be used for fetal assessment (e.g., birth weight estimation). Based on the generated data, users (e.g., doctors) may investigate further, such as for particular conditions or possible health risks (e.g., macrosomia, Intrauterine growth restriction (IUGR), etc.) to avoid severe complications and avoid adverse outcome for the mother and her child.

Figure 3:
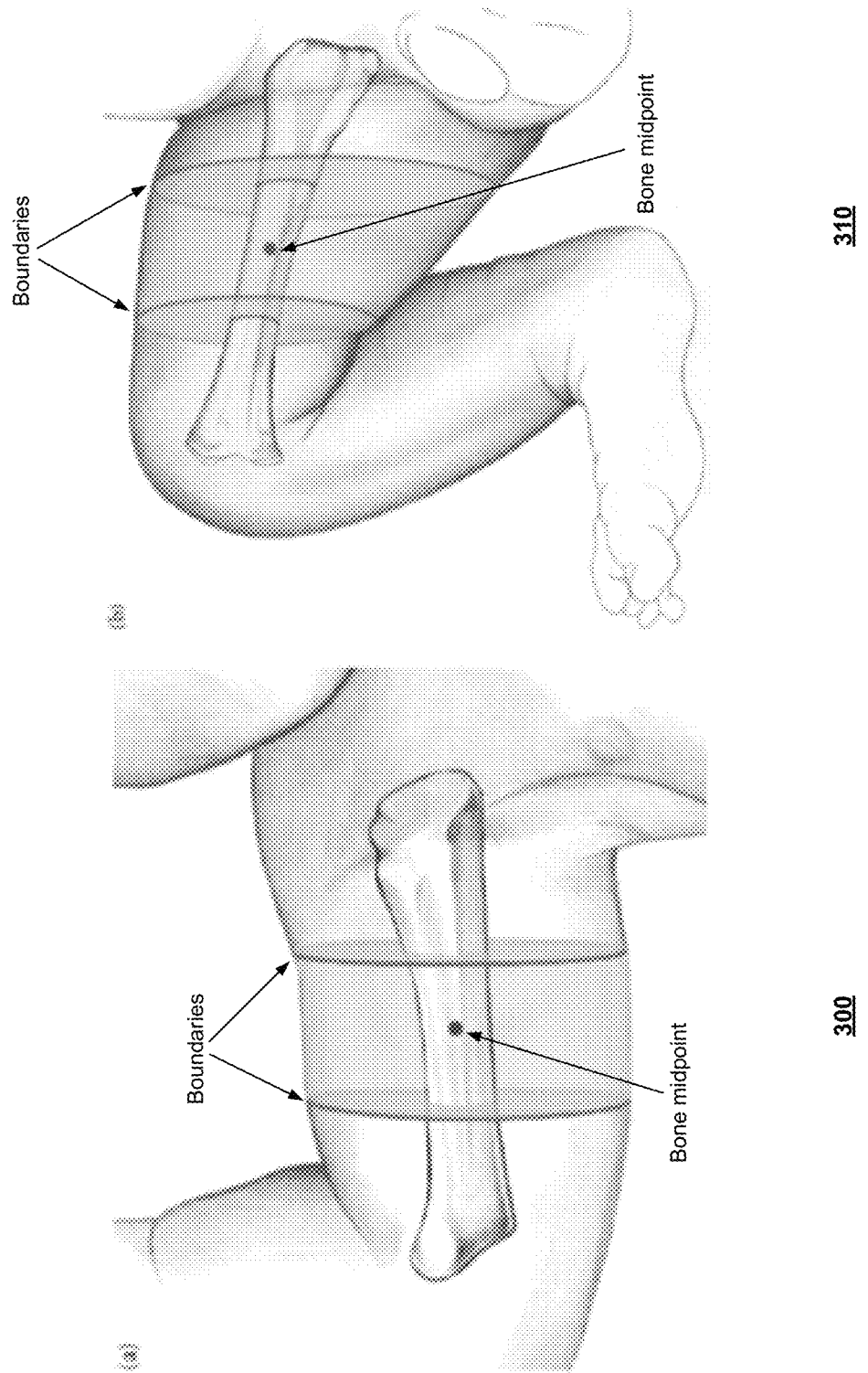
FIG. 3 illustrates example fractional limb volumes.

FIG. 3 illustrates example fractional limb volumes. Shown in FIG. 3 fractional arm volume (AVol) 310 and fractional thigh volume (TVol) 320. Fractional limb volume (FLV) is a soft tissue parameter that derived from a central portion of the limb diaphysis, which may be used for evaluation of fetal nutritional status.

The fractional arm volumes (AVol) and the fractional thigh volumes (TVol) are generated based on particular bone(s) in the limb—e.g., the humerus bone for the fractional arm volumes and the Femur bone for the fractional thigh volume. Typically, fractional arm (AVol) and thigh (TVol) volumes are determined based on 50% of the humeral or femoral diaphysis length. For example, once the mid-point of the bone is determined, the boundaries of the volume are set (on either side of the mid-point, as shown in FIG. 3) so that 50% of the mass is included in the volume. The fetal assessment can be made more comprehensive by taking into account the soft tissue parameters. Fractional limb volumes may be obtained in the course of medical imaging examination of the fetus, such as based on images generated and displayed during such examination. An example ultrasound-based use case scenario is shown in FIG. 4.

Figure 4:
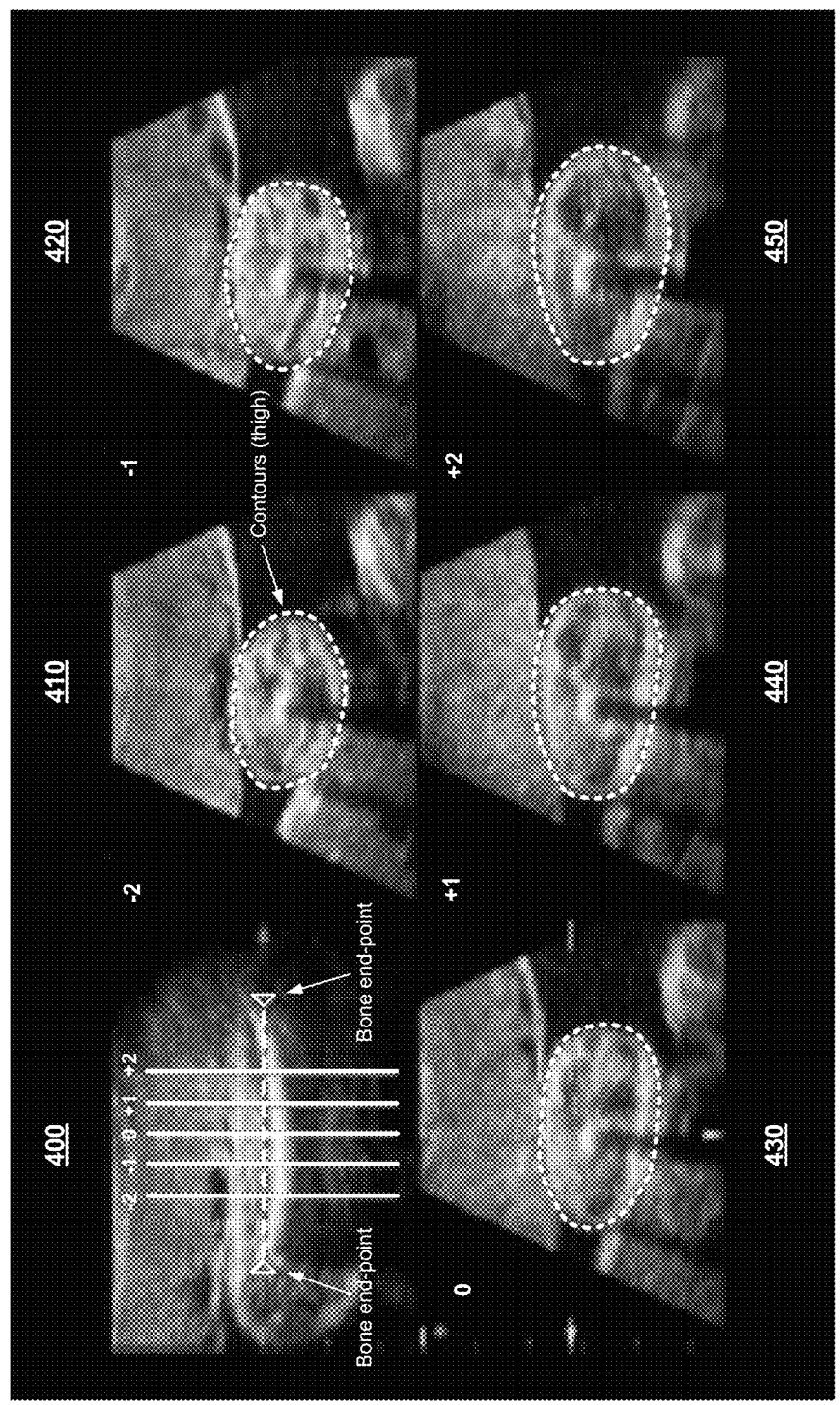
FIG. 4 illustrates example use case for generating cross-section limb slices for fractional limb volume analysis based on ultrasound scanning.

FIG. 4 illustrates example use case for generating cross-section limb slices for fractional limb volume analysis based on ultrasound scanning. Shown in FIG. 4 is a sequence of ultrasound images (400-450) during ultrasound-based fractional thigh volume (TVol) based analysis.

The ultrasound images (or imaging dataset corresponding thereto) may be obtained via a suitable system, such as the ultrasound imaging system 200 of FIG. 2. Ultrasound image 400 corresponds to an ultrasound scan of a fetus, and particularly the fetus' thigh. The fractional thigh volume (TVol) analysis may be performed using and starting with image 400. In this regard, such analysis is done manually by the user (e.g., clinician or obstetrician). In particular, once the ultrasound image is generated and displayed, the user may first identify and mark the end-points of the bone as the bone is visible during the scan. Based on the marked bone endpoints, the bone mid-point is identified and marked (shown as plane/line 0 in image 400).

Once the bone mid-point is identified and marked, the two outer slices having inter-slice distance as 50% of the bone length between them and equidistant from mid-point may be identified and set on either side of the bone mid-point (shown as planes/lines −2 and +2 in image 400). The volume in-between the two outer slices is then further sliced (e.g., at the mid-point on each side), thus resulting two additional slices have inter-slice distance as 25% of the bone length between them and lie on either side of the bone mid-point (shown as planes/lines −1 and +1 in image 400). Thus, a number of slices may be identified and marked (e.g., 5 in image 400, corresponding to planes/lines −2, −1, 0, +1, and +2).

Next, cross-section scans at each of these slices (shown as images/scans 410, 420, 430, 440 and 450 in FIG. 4) may be generated and analyzed. In this regard, analysis of each cross-section scan may entail identifying and marking the outer contours of the thigh at each of these slices, as shown in FIG. 4. An example cross-section based analysis is described in more detail with respect to FIG. 5.

Figure 5:
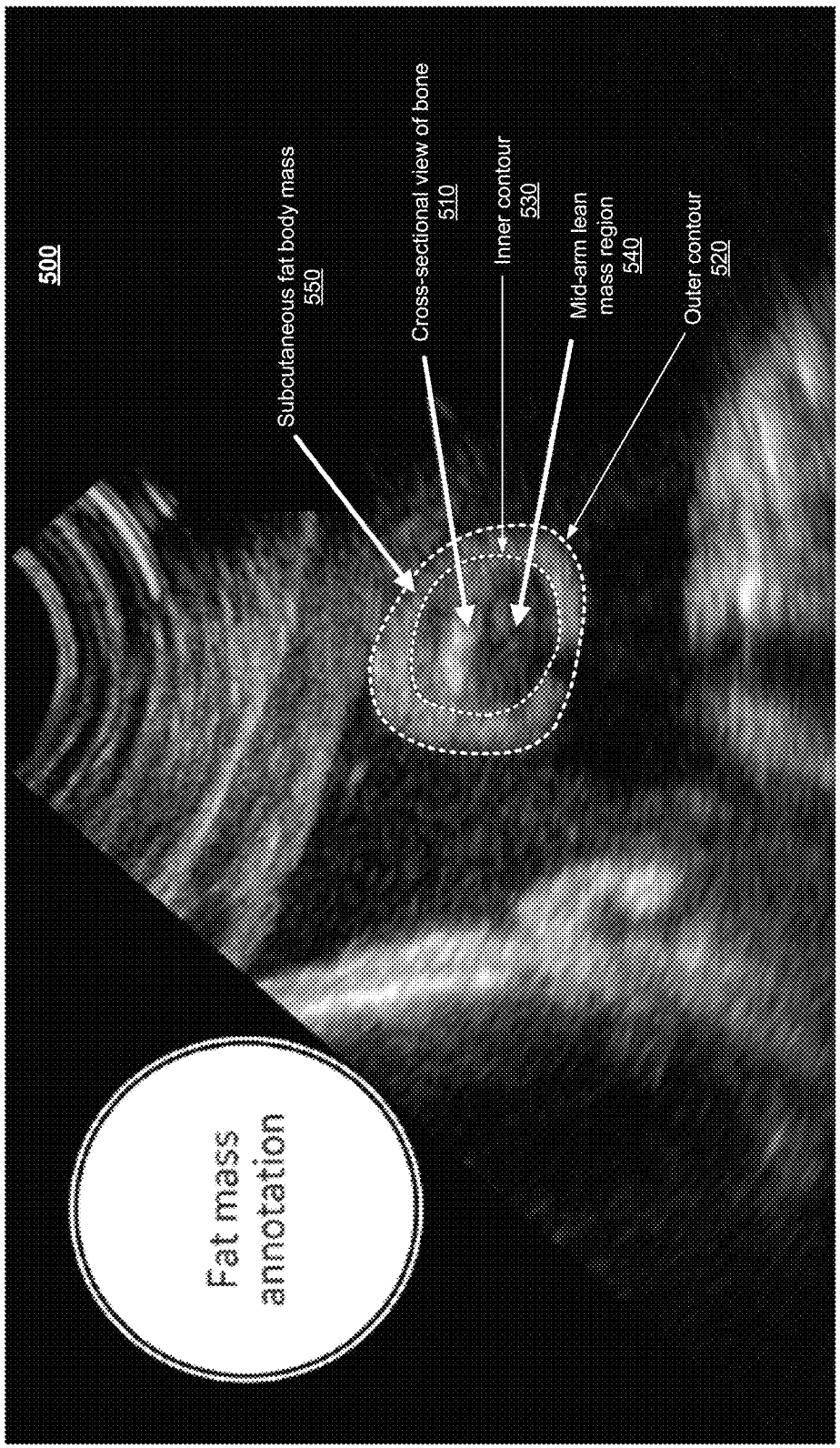
FIG. 5 illustrates sonographic view of fetal limb cross-section during example fractional limb volume analysis.

FIG. 5 illustrates sonographic view of fetal arm cross-section during example fractional arm volume analysis. Shown in FIG. 5 is an ultrasound image 500, which may be generated and displayed for fetal limb cross-section, such as during fractional limb volume (FLV) analysis.

The ultrasound image 500 (or imaging dataset corresponding thereto) may be generated using a suitable system, such as the ultrasound imaging system 200 of FIG. 2. In this regard, ultrasound image 500 corresponds to an ultrasound scan of a fetus, and particularly the fetus' arm during fractional arm volume (AVol) analysis. In particular, ultrasound image 500 refers to a fetal arm cross-section (e.g., based on particular slice at some point in the bone, such as the mid-point, one of the two 25% bone length points, or one of the two 50% bone length points). Identified and marked in the image 500 are the cross-sectional view of bone 510 within that slice, and the outer contour 520, which represents the mid-arm circumference, and the inner contour 530, which encircles the mid-arm lean mass 540, which comprises the bone and the non-fat tissues around it (e.g., muscles, etc.). Thus, the region between outer contour 520 and the inner contour 530 is the mid-arm fat mass (or subcutaneous fat body mass) 550.

Measurements obtained based on mid-arm volume analysis (particularly the mid-arm lean mass 540 and the mid-arm fat mass 550) may then be used in allows in assessing fetal health and nutritional status. While several alternative mythologies (e.g., head, abdominal and femoral diaphysis length) may be used for estimation of birth weight, mid-arm based analysis may be more desirable. This may be the case because mid-arm circumference may be more useful than bone length and head circumference for identifying growth restriction. In this regard, rapid changes in soft tissue accretion, especially during the third trimester of pregnancy, could provide the basis for a sensitive biomarker of fetal growth aberrations by allowing direct comparisons between fractional limb volume measurements and cross-sectional standards.

However, as noted fractional limb volume based analysis may have some limitations and/or may pose some challenges. For example, in convention solutions, most of the steps and actions during fractional limb analysis are done manually. Solutions in accordance with the present disclosure may overcome and remedy many of these limitations and challenges.

In particular, implementations in accordance with the present disclosure incorporate a computational approach for automatic assessment of fractional limb volume followed by estimation of fat lean mass of fetus from medical scans (e.g., 3D ultrasound image). The evaluation of both fractional limb volume and fat lean mass may be performed using artificial intelligence, such as using deep learning networks which require minimum manual intervention on part of the user (e.g., sonographer). The two assessments may be done sequentially, and the intermediate output (e.g., segmentation map) may be generated during the estimation of fractional limb volume is used as a prior for evaluation of fat lean mass.

Accordingly, implementations in accordance with the present disclosure may have various unique and distinguishing features, particularly compared to any existing solution. In particular, automatic assessment of both fractional limb volume and fat lean mass are used and implemented in a cascaded manner. Also, deep learning may be used as the primary algorithm for both assessment estimations, and is similarly used in cascaded fashion. Further, the use of intermediate output during calculation of fractional limb volume helps in improving the calculation of fat lean mass in the next stage. Thus, the intermediate output may be fed as an input to the deep learning model used for estimation of fat lean mass. Such cascading is also unique from the perspective of deep learning modelling. In this regard, rather than use fixed shape priors created via manual annotation, solutions in accordance with the present disclosure incorporate use of prior estimates (obtained through one deep learning model) in improving performance of segmentation via another deep learning model.

Figure 6:
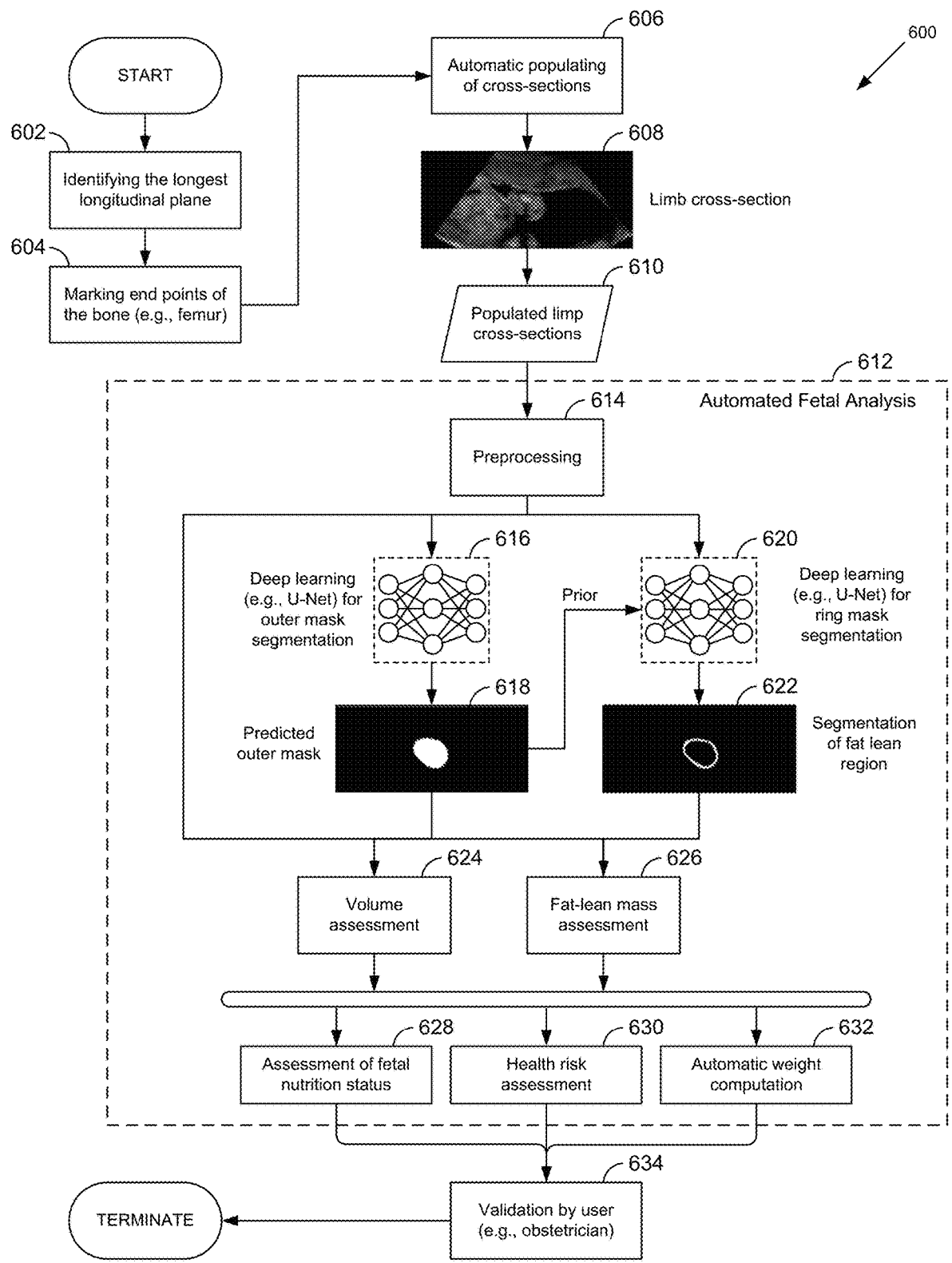
FIG. 6 illustrates a flowchart of an example process for automatic assessment of fractional limb volume and fat lean mass from fetal medical images.

FIG. 6 illustrates a flowchart of an example process for automatic assessment of fractional limb volume and fat lean mass from fetal medical images. Shown in FIG. 6 is flow chart 600, comprising a plurality of example steps (represented as blocks 602-632), which may be performed in a suitable system (e.g., the medical imaging system 110 of FIG. 1, the ultrasound imaging system 200 of FIG. 2, etc.) automatic assessment of fractional limb volume and fat lean mass from fetal medical images (e.g., fetal three-dimensional (3D) ultrasound scans).

After start step, in which the system may be setup, and operations may initiate to obtain and generate medical image (e.g., ultrasound images, as described with respect to FIG. 2), in step 602, the longest longitudinal plane may be identified in the limb (e.g., as illustrated in image 400 in FIG. 4). In step 604, end-points of the bone (e.g., femur) may be identified and marked. In step 606, automatic populating of cross-sections which may be performed. This may include an automatic determination of a number of cross-sectional planes, such as based on identification of the bone mid-point and a corresponding number of planes/slices based on the bone mid-point—e.g., corresponding to 50% and 25% of limb bone length, similar to what is shown in FIG. 4 but done automatically. In step 608, a number of limb cross-section images, corresponding to the identified cross-sectional planes, may be obtained or generated, such as based on the three-dimensional (3D) dataset. In step 610, limb cross-sections may be populated (e.g., as described with respect to FIG. 5, for each cross-section plane/slice).

The automated fetal analysis 612 may then be performed (encompassing all the steps and actions shown within the dashed block in FIG. 6). In this regard, the automated fetal analysis 612 may be performed (in whole or in part) in the same system used in obtaining or generating the medical imaging (e.g., ultrasound scan); alternatively, at least a portion of automated fetal analysis 612 may be performed in a separate system, which may be local or remote relative to the imaging system.

In step 614, preprocessing of the limb cross-sections may be performed. This may comprise configuring data for use in deep learning models based on the populated limb cross-sections related information. In step 616, a deep learning model for outer mask segmentation may be applied, using as input data obtained from the preprocessing at step 614. In step 618, a predicted outer mask—that is, predication of applicable outer contour—for each cross-section) may be generated based on applying of the outer mask segmentation deep learning model. In step 620, a deep learning model for ring mask segmentation may be applied, using as input data obtained from the preprocessing at step 614 as well as data based on the predicted outer mask as determined in step 618. In step 622, a segmentation of fat lean region (for each cross-section) may be generated based on applying of the ring mask segmentation deep learning model. Thus, the deep learning model applied in step 620 may allow for determination of fat-lean segmentation to determine the inner contours based on the cross-section data and the predicted outer counters as determined in step(s) 618 based on application of the deep learning model in step 616. The deep learning models may be of any suitable type. For example, in some implementations, U-Nets may be used. In this regard, a U-Net comprises a convolutional neural network that configured for biomedical image segmentation.

In steps 624, volume assessment may be performed (for each cross-section), using the corresponding predicted outer mask (as determined in step 618) and segmentation of fat lean region (as determined in step 622), as well as based on data obtained from the preprocessing at step 614. Similarly, in step 626, fat-lean mass assessment may be performed. As noted, both of these assessments are performed automatically in the system, and in cascaded manner.

Various fetal related assessments may then be performed. For example, in step 628, assessment of fetal nutrition status may be performed. In step 630, health risk assessment may be performed. In step 632, weight computation may be performed. These assessments may be performed using and based on output of the volume assessment (as determined in step 624) and fat-lean mass assessment (as determined in step 626). Further, as noted, both of these assessments are performed automatically in the system, and (at least in some instances) in cascaded manner.

In step 634, output of the automated fetal analysis, particularly the results and information corresponding to the fetal assessments (e.g., steps 628-632) may be validated by the user (e.g., obstetrician). The process may then terminate.

Solutions in accordance with the present disclosure may have various technical and commercial advantages over any existing convention solutions. For example, solutions in accordance with the present disclosure (e.g., using the automated analysis as describe above) may greatly reduce time (e.g., up to 5 times) needed for completing the fetal assessments compared to conventional solutions which may require completing at least some of the steps (e.g., contouring of each cross-section slices) manually by the user. In this regard the contouring process may be drastically sped up by using the automated and deep learning based segmentation of the soft tissue.

Solutions in accordance with the present disclosure (e.g., using the automated analysis as describe above) may also improve efficiency. For example, manual annotation of cross-section slices is a very tedious and laborious process, and requires significant amount of expertise for annotating the samples. Thus, use of the solutions in accordance with the present disclosure may be particularly advantageous even in resource limited settings and/or with scarcity of expertise, to still ensure reliably diagnosing ultrasound scans and providing proper assessments even by semi-skilled users.

Further, solutions in accordance with the present disclosure (e.g., using the automated analysis as describe above) may allow for early diagnosis and clinical decision making. In this regard, in some implementations maternal and fetal health risks may be identified and various critical conditions may be diagnosed. The proposed solutions may also help doctor validate this diagnosis and aid doctors in decision making.

An example method for automatic assessment of fractional limb volume and fat lean mass from fetal medical imaging, in accordance with the present disclosure, comprises: applying automated assessment for a fetus based on imaging data obtained during medical imaging examination of the fetus, wherein the applying the automated assessment comprises: processing imaging data corresponding to a plurality of a cross-section imaging slices corresponding to a limb of the fetus, wherein the processing comprises for each imaging slice: automatically generating a predicted outer mask corresponding to contour of the limb cross-section based on application of a first pre-trained model to imaging data corresponding to the imaging slice; and automatically generating a segmentation of fat-lean region for the imaging slice based on application of a second pre-trained model to both of the imaging data corresponding to the imaging slice and the generated predicted outer mask; and applying based on the processing of the imaging data corresponding to the plurality of a cross-section imaging slices: a fractional limb volume assessment; and a fat-lean mass assessment.

In an example embodiment, each of the first pre-trained model and the second pre-trained model comprises artificial intelligence (AI) based model.

In an example embodiment, the method further comprises automatically applying, based on one or both of the fractional limb volume assessment and the fat-lean mass assessment, one or more of a plurality of fetus related assessments, the plurality of plurality of fetus related assessments comprising at least weight computation, high risk assessment, and fetal nutrition status.

In an example embodiment, the method further comprises processing the imaging data obtained during the medical imaging examination of the fetus, wherein the processing of the imaging data comprises Identifying a longest longitudinal plane within the limb of the fetus.

In an example embodiment, the processing of the imaging data further comprises identifying a bone in the limb, and marking end-points of the identified bone.

In an example embodiment, the method further comprises determining the plurality of a cross-section imaging slices based on the identified bone.

In an example embodiment, determining the plurality of a cross-section imaging slices based on the identified bone comprises: identifying a mid-point of the identified bone; setting one slice of the plurality of cross-section imaging slices at the mid-point of the identified bone; and setting one or more pairs of equidistant slices centered around the mid-point of the identified bone.

An example non-transitory computer readable medium in accordance with the present disclosure has stored thereon a computer program having at least one code section, the at least one code section being executable by a machine comprising at least one processor, for causing the machine to perform one or more steps comprising: applying automated assessment for a fetus based on imaging data obtained during medical imaging examination of the fetus, wherein the applying the automated assessment comprises: processing imaging data corresponding to a plurality of a cross-section imaging slices corresponding to a limb of the fetus, wherein the processing comprises for each imaging slice: automatically generating a predicted outer mask corresponding to the contour of the limb cross-section based on application of a first pre-trained model to imaging data corresponding to the imaging slice; and automatically generating a segmentation of fat-lean mask for the imaging slice based on application of a second pre-trained model to both of the imaging data corresponding to the imaging slice and the generated predicted outer mask; and applying based on the processing of the imaging data corresponding to the plurality of a cross-section imaging slices: a fractional limb volume assessment; and a fat-lean mass assessment.

In an example implementation, each of the first pre-trained model and the second pre-trained model comprises artificial intelligence (AI) based model.

In an example implementation, the one or more steps further comprise automatically applying, based on one or both of the fractional limb volume assessment and the fat-lean mass assessment, one or more of a plurality of fetus related assessments, the plurality of plurality of fetus related assessments comprising at least weight computation, high risk assessment, and fetal nutrition status.

In an example implementation, the one or more steps further comprise processing the imaging data obtained during the medical imaging examination of the fetus, wherein the processing of the imaging data comprises Identifying a longest longitudinal plane within the limb of the fetus.

In an example implementation, the processing of the imaging data further comprises identifying a bone in the limb, and marking end-points of the identified bone.

In an example implementation, the one or more steps further comprise determining the plurality of a cross-section imaging slices based on the identified bone.

In an example implementation, determining the plurality of a cross-section imaging slices based on the identified bone further comprises: identifying a mid-point of the identified bone; setting one slice of the plurality of cross-section imaging slices at the mid-point of the identified bone; and setting one or more pairs of equidistant slices centered around the mid-point of the identified bone.

An example system, for automatic assessment of fractional limb volume and fat lean mass from fetal medical imaging, in accordance with the present disclosure, comprises one or more processing circuits are configured to apply automated assessment for a fetus based on imaging data obtained during medical imaging examination of the fetus, wherein the applying the automated assessment comprises: processing imaging data corresponding to a plurality of a cross-section imaging slices corresponding to a limb of the fetus, wherein the processing comprises for each imaging slice: automatically generating a predicted outer mask for an outer contour of the limb based on application of a first pre-trained model to imaging data corresponding to the imaging slice; and automatically generating a segmentation of fat-lean mask for the imaging slice based on application of a second pre-trained model to both of the imaging data corresponding to the imaging slice and the generated predicted output mask; and applying based on the processing of the imaging data corresponding to the plurality of a cross-section imaging slices: a fractional limb volume assessment; and a fat-lean mass assessment; wherein each of the first pre-trained model and the second pre-trained model comprises artificial intelligence (AI) based model.

In an example implementation, the one or more processing circuits are further configured to automatically apply, based on one or both of the fractional limb volume assessment and the fat-lean mass assessment, one or more of a plurality of fetus related assessments, the plurality of plurality of fetus related assessments comprising at least weight computation, high risk assessment, and fetal nutrition status.

In an example implementation, the one or more processing circuits are further configured to process the imaging data obtained during the medical imaging examination of the fetus, wherein the processing of the imaging data comprises Identifying a longest longitudinal plane within the limb of the fetus.

In an example implementation, the one or more processing circuits are further configured to, when processing the imaging data, identify a bone in the limb, and marking end-points of the identified bone.

In an example implementation, the one or more processing circuits are further configured to determine the plurality of a cross-section imaging slices based on the identified bone.

In an example implementation, the one or more processing circuits are further configured to, when determining the plurality of a cross-section imaging slices based on the identified bone: identify a mid-point of the identified bone; set one slice of the plurality of cross-section imaging slices at the mid-point of the identified bone; and set one or more pairs of equidistant slices centered around the mid-point of the identified bone.

As utilized herein the terms "circuits" and "circuitry" refer to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z." As utilized herein, the terms "block" and "module" refer to functions than can be performed by one or more circuits. As utilized herein, the term "exemplary" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware (and code, if any is necessary) to perform the function, regardless of whether performance of the function is disabled or not enabled (e.g., by some user-configurable setting, a factory trim, etc.).

Other embodiments of the invention may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

Accordingly, the present disclosure may be realized in hardware, software, or a combination of hardware and software. The present invention may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

Various embodiments in accordance with the present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method comprising:
applying automated assessment for a fetus based on imaging data obtained during medical imaging examination of the fetus, wherein the applying the automated assessment comprises:
processing imaging data corresponding to a plurality of a cross-section imaging slices corresponding to a limb of the fetus, wherein the processing comprises for each imaging slice:
automatically generating a predicted outer mask corresponding to contour of the limb cross-section based on application of a first pre-trained model to imaging data corresponding to the imaging slice; and
automatically generating a segmentation of fat-lean region for the imaging slice based on application of a second pre-trained model to both of the imaging data corresponding to the imaging slice and the generated predicted outer mask; and
applying based on the processing of the imaging data corresponding to the plurality of the cross-section imaging slices:
a fractional limb volume assessment; and
a fat-lean mass assessment.

2. The method of claim 1, wherein each of the first pre-trained model and the second pre-trained model comprises artificial intelligence (AI) based model.

3. The method of claim 1, further comprising automatically applying, based on one or both of the fractional limb volume assessment and the fat-lean mass assessment, one or more of a plurality of fetus related assessments, the plurality of plurality of fetus related assessments comprising at least weight computation, high risk assessment, and fetal nutrition status.

4. The method of claim 1, further comprising processing the imaging data obtained during the medical imaging examination of the fetus, wherein the processing of the imaging data comprises identifying a longest longitudinal plane within the limb of the fetus.

5. The method of claim 4, wherein the processing of the imaging data further comprises identifying a bone in the limb, and marking end-points of the identified bone.

6. The method of claim 5, further comprising determining the plurality of the cross-section imaging slices based on the identified bone.

7. The method of claim 6, wherein determining the plurality of the cross-section imaging slices based on the identified bone comprises:
identifying a mid-point of the identified bone;
setting one slice of the plurality of cross-section imaging slices at the mid-point of the identified bone; and
setting one or more pairs of equidistant slices centered around the mid-point of the identified bone.

8. A non-transitory computer readable medium having stored thereon a computer program having at least one code section, the at least one code section being executable by a machine comprising at least one processor, for causing the machine to perform one or more steps comprising:

applying automated assessment for a fetus based on imaging data obtained during medical imaging examination of the fetus, wherein the applying the automated assessment comprises:

processing imaging data corresponding to a plurality of a cross-section imaging slices corresponding to a limb of the fetus, wherein the processing comprises for each imaging slice:

automatically generating a predicted outer mask corresponding to the contour of the limb cross-section based on application of a first pre-trained model to imaging data corresponding to the imaging slice; and automatically generating a segmentation of fat-lean region for the imaging slice based on application of a second pre-trained model to both of the imaging data corresponding to the imaging slice and the generated predicted outer mask; and applying based on the processing of the imaging data corresponding to the plurality of the cross-section imaging slices:
a fractional limb volume assessment; and
a fat-lean mass assessment.

9. The non-transitory computer readable medium of claim 8, wherein each of the first pre-trained model and the second pre-trained model comprises artificial intelligence (AI) based model.

10. The non-transitory computer readable medium of claim 8, wherein the one or more steps further comprise automatically applying, based on one or both of the fractional limb volume assessment and the fat-lean mass assessment, one or more of a plurality of fetus related assessments, the plurality of plurality of fetus related assessments comprising at least weight computation, high risk assessment, and fetal nutrition status.

11. The non-transitory computer readable medium of claim 8, wherein the one or more steps further comprise processing the imaging data obtained during the medical imaging examination of the fetus, wherein the processing of the imaging data comprises Identifying a longest longitudinal plane within the limb of the fetus.

12. The non-transitory computer readable medium of claim 11, wherein the processing of the imaging data further comprises identifying a bone in the limb, and marking end-points of the identified bone.

13. The non-transitory computer readable medium of claim 12, wherein the one or more steps further comprise determining the plurality of the cross-section imaging slices based on the identified bone.

14. The non-transitory computer readable medium of claim 13, wherein determining the plurality of the cross-section imaging slices based on the identified bone comprises:
identifying a mid-point of the identified bone;
setting one slice of the plurality of cross-section imaging slices at the mid-point of the identified bone; and
setting one or more pairs of equidistant slices centered around the mid-point of the identified bone.

15. A system comprising:
one or more processing circuits are configured to apply automated assessment for a fetus based on imaging data obtained during medical imaging examination of the fetus, wherein the applying the automated assessment comprises:

processing imaging data corresponding to a plurality of a cross-section imaging slices corresponding to a limb of the fetus, wherein the processing comprises for each imaging slice:

automatically generating a predicted outer mask corresponding to the contour of the limb cross-section based on application of a first pre-trained model to imaging data corresponding to the imaging slice; and automatically generating a segmentation of fat-lean mask for the imaging slice based on application of a second pre-trained model to both of the imaging data corresponding to the imaging slice and the generated predicted outer mask; and applying based on the processing of the imaging data corresponding to the plurality of the cross-section imaging slices:
a fractional limb volume assessment; and
a fat-lean mass assessment;
wherein each of the first pre-trained model and the second pre-trained model comprises artificial intelligence (AI) based model.

16. The system of claim 15, wherein the one or more processing circuits are further configured to automatically apply, based on one or both of the fractional limb volume assessment and the fat-lean mass assessment, one or more of a plurality of fetus related assessments, the plurality of plurality of fetus related assessments comprising at least weight computation, high risk assessment, and fetal nutrition status.

17. The system of claim 15, wherein the one or more processing circuits are further configured to process the imaging data obtained during the medical imaging examination of the fetus, wherein the processing of the imaging data comprises Identifying a longest longitudinal plane within the limb of the fetus.

18. The system of claim 17, wherein the one or more processing circuits are further configured to, when processing the imaging data, identify a bone in the limb, and marking end-points of the identified bone.

19. The system of claim 18, wherein the one or more processing circuits are further configured to determine the plurality of the cross-section imaging slices based on the identified bone.

20. The system of claim 19, wherein the one or more processing circuits are further configured to, when determining the plurality of the cross-section imaging slices based on the identified bone:
identify a mid-point of the identified bone;
set one slice of the plurality of cross-section imaging slices at the mid-point of the identified bone; and
set one or more pairs of equidistant slices centered around the mid-point of the identified bone.

* * * * *